US00PP23652P2

(12) United States Plant Patent
Schenk

(10) Patent No.: US PP23,652 P2
(45) Date of Patent: Jun. 4, 2013

(54) LILY PLANT NAMED 'SUNNY CYPRES'

(50) Latin Name: ***Lilium* L.**
Varietal Denomination: Sunny Cypres

(75) Inventor: Pieter Cornelis Schenk, Wieringerwerf (NL)

(73) Assignee: Mak Breeding Rights B.V., Wieringerwerf (NL)

( * ) Notice: Subject to any disclaimer, the term of this patent is extended or adjusted under 35 U.S.C. 154(b) by 137 days.

(21) Appl. No.: 13/134,376

(22) Filed: Jun. 6, 2011

(51) Int. Cl.
*A01H 5/00* (2006.01)

(52) U.S. Cl.
USPC ..... Plt./315

(58) Field of Classification Search ..... Plt./315
See application file for complete search history.

*Primary Examiner* — June Hwu
(74) *Attorney, Agent, or Firm* — C. A. Whealy

(57) ABSTRACT

A new and distinct cultivar of Lily plant named 'Sunny Cypres', characterized by its upright and compact plant habit; vigorous growth habit; densely-foliated habit; freely flowering habit; upright flower buds; white and light red purple-colored flowers; and good postproduction longevity.

1 Drawing Sheet

Botanical designation: *Lilium* L.
Cultivar denomination: 'SUNNY CYPRES'.

BACKGROUND OF THE INVENTION

The present Invention relates to a new and distinct cultivar of Lily plant, commercially known as Oriental Hybrid Lily, botanically known as *Lilium* L. and hereinafter referred to by the name 'Sunny Cypres'.

The new Oriental Hybrid Lily plant is a product of a planned breeding program conducted by the Inventor in Wieringerwerf, The Netherlands. The objective of the breeding program is to develop new compact and dense potted Oriental Hybrid Lily plants with large flowers, attractive flower coloration and good postproduction longevity.

The new Oriental Hybrid Lily plant originated from a cross-pollination in 2001 of an unnamed proprietary selection of *Lilium* L., not patented, as the female, or seed, parent with an unnamed proprietary selection of *Lilium* L., not patented, as the male, or pollen, parent. The new Oriental Hybrid Lily plant was discovered and selected by the Inventor as a single flowering plant from within the resultant progeny of the cross-pollination in a controlled greenhouse environment in Wieringerwerf, The Netherlands in July, 2005.

Asexual reproduction of the new Oriental Hybrid Lily plant by bulb scales in a controlled greenhouse environment in Wieringerwerf, The Netherlands since November, 2006, has shown that the unique features of this new Oriental Hybrid Lily plant are stable and reproduced true to type in successive generations.

SUMMARY OF THE INVENTION

Plants of the new Oriental Hybrid Lily have not been observed under all possible environmental conditions. The phenotype may vary somewhat with variations in environment such as temperature and light intensity without, however, any variance in genotype.

The following traits have been repeatedly observed and are determined to be the unique characteristics of 'Sunny Cypres'. These characteristics in combination distinguish 'Sunny Cypres' as a new and distinct cultivar of Oriental Hybrid Lily plant:

1. Upright and compact plant habit.
2. Vigorous growth habit.
3. Densely-foliated habit.
4. Freely flowering habit.
5. Upright flower buds.
6. White and light red purple-colored flowers.
7. Good postproduction longevity.

Plants of the new Oriental Hybrid Lily differ primarily from plants of the female parent selection primarily in the following characteristics:

1. Plants of the new Oriental Hybrid Lily have larger leaves than plants of the female parent selection.
2. Plants of the new Oriental Hybrid Lily and the female parent selection differ slightly in flower color.

Plants of the new Oriental Hybrid Lily differ primarily from plants of the male parent selection primarily in the following characteristics:

1. Plants of the new Oriental Hybrid Lily have larger flowers than plants of the male parent selection.
2. Plants of the new Oriental Hybrid Lily and the male parent selection differ in flower color as plants of the male parent selection have pink-colored flowers.

Plants of the new Oriental Hybrid Lily can be compared to plants of Oriental Hybrid Lily 'Sunny Bonaire', not patented. Plants of the new Oriental Hybrid Lily differ from plants of 'Sunny Bonaire' in the following characteristics:

1. Plants of the new Oriental Hybrid Lily are taller than plants of 'Sunny Bonaire'.
2. Plants of the new Oriental Hybrid Lily have larger flowers than plants of 'Sunny Bonaire'.
3. Under warm conditions, flower color of plants of the new Oriental Hybrid Lily does not fade whereas flower color of plants of 'Sunny Bonaire' fades under warm conditions.

DESCRIPTION OF THE PHOTOGRAPH

The accompanying colored photograph illustrates the overall appearance of the new Oriental Hybrid Lily plant showing the colors as true as it is reasonably possible to obtain in colored reproductions of this type. Colors in the photograph may differ slightly from the color values cited in the detailed botanical description which accurately describe the colors of the new Oriental Hybrid Lily plant. The photograph comprises a side perspective view of a typical flowering plant of 'Sunny Cypres' grown in a container.

DETAILED BOTANICAL DESCRIPTION

The aforementioned photograph and following observations and measurements describe plants that were grown during the spring in 15-cm containers in a glass-covered greenhouse in Wieringerwerf, The Netherlands and under cultural conditions typically used in Oriental Hybrid Lily production. During the production of the plants, day temperatures averaged 15° C., night temperatures averaged 18° C. and light levels averaged 6,000 lux. Measurements and numerical values represent averages for typical flowering plants. Plants were 110 days old when the photograph and description were taken. In the following description, color references are made to The Royal Horticultural Society Colour Chart, 2001 Edition, except where general terms of ordinary dictionary significance are used.

Botanical classification: *Lilium* L. 'Sunny Cypres'.

Parentage:

*Female, or seed, parent*.—Unnamed proprietary selection of *Lilium* L., not patented.

*Male, or pollen, parent*.—Unnamed proprietary selection of *Lilium* L., not patented.

Plant description:

*Plant form and growth habit*.—Upright flowering plant; single erect flowering stem with a terminal cluster of flowers; compact and dense plant habit; vigorous growth habit.

*Plant height, soil level to top of flowers*.—About 47 cm.

*Plant circumference*.—About 75 cm.

*Bulbs*.—Diameter: About 10 cm to 20 cm. Texture: Smooth. Color: Close to 155D.

*Flowering stems*.—Diameter: About 1 cm. Internode length: About 6 mm to 7 mm. Strength: Strong. Texture: Smooth, glabrous. Color: Towards the apex, close to 138A; towards the base, close to 138B.

*Leaves*.—Arrangement and quantity: Alternate; simple; sessile; about 40 leaves per plant. Length, lower leaves: About 10 cm. Width, lower leaves: About 3.5 cm. Length, upper leaves: About 17 cm. Width, upper leaves: About 6.5 cm. Shape: Lanceolate. Apex: Acute. Base: Decurrent. Margin: Entire. Texture, upper and lower surfaces: Glabrous, smooth; leathery. Venation pattern: Parallel. Color: Developing and fully expanded leaves, upper surface: Close to 147A; venation, close to 147A. Developing and fully expanded leaves, lower surface: Close to 147B; venation, close to 147B.

Flower description:

*Flower arrangement*.—Flowers umbellate.

*Flower shape and aspect*.—Flowers are funnel-shaped and when fully opened, flatten and recurve towards the apex; flower buds face upright and flowers face upright to outwardly.

*Flowering habit*.—Freely flowering habit, large bulbs will produce five to eight flowers per flowering stem.

*Fragrance*.—Slightly fragrant.

*Natural flowering season*.—Plants flower in June and July in The Netherlands; plants can be flowered year-round in the greenhouse and forced to bloom about 110 days after planting bulbs.

*Postproduction longevity*.—Good postproduction longevity, flowers last about two weeks on the plant; tepals not persistent; gynoecium persistent.

*Flower buds*.—Length: About 11 cm. Diameter: About 3.5 cm. Circumference: About 10 cm. Shape: Lanceolate. Color: Close to 145B; sutures, close to 145B and 150B.

*Flower size*.—Diameter: About 20 cm. Length (height): About 8 cm.

*Perianth*.—Quantity/arrangement: Six tepals per flower; tepals imbricate. Tepal length, inner tepals: About 11.5 cm. Tepal width, inner tepals: About 6 cm. Tepal length, outer tepals: About 12 cm. Tepal width, outer tepals: About 4.5 cm. Tepal shape: Lanceolate. Tepal apex: Acute. Tepal margin: Entire. Tepal texture, upper and lower surfaces: Smooth, glabrous. Tepal color: When opening, upper and lower surfaces: Close to 155D; towards the center and apex, tinted with close to 65B. Fully opened, upper and lower surfaces: Close to 65B.

*Pedicels*.—Angle: About 30° to 45° from vertical. Strength: Strong. Length: About 2.5 cm. Diameter: About 2 mm. Texture: Smooth, glabrous. Color: Close to 143A.

*Reproductive organs*.—Stamens: Quantity per flower: About six. Filament length: About 7.5 cm. Filament color: Between 155D and 145D. Anther length: About 1.5 cm. Anther color: Close to 24C. Pollen color: Close to 175C. Pistils: Quantity per flower: One. Pistil color: Close to 184C. Style length: About 8 cm. Style color: Close to 144B.

*Fruits*.—Length: About 2 cm. Diameter: About 5 mm. Color: Close to 144B.

*Seed produced*.—No viable seeds observed.

Disease/pest resistance: Resistance to pathogens and pests common to Oriental Lilies has not been observed.

Garden performance: Plants of the new Oriental Hybrid Lily have exhibited good tolerance to rain and wind and have been observed to tolerate temperatures from about −2° C. to about 40° C.

It is claimed:

1. A new and distinct Lily plant named 'Sunny Cypres' as illustrated and described.

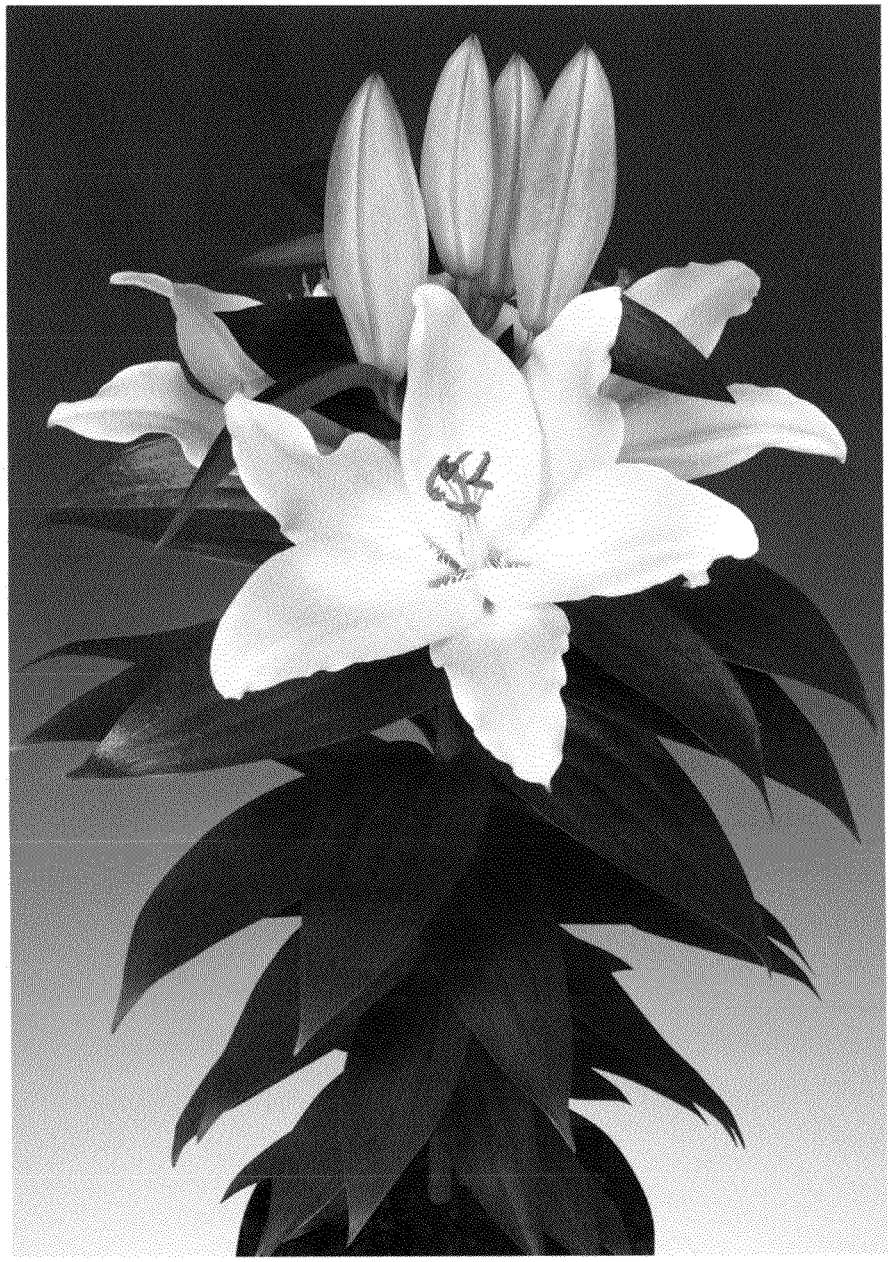

* * * * *